US007005126B1

(12) United States Patent
Link, Jr. et al.

(10) Patent No.: US 7,005,126 B1
(45) Date of Patent: *Feb. 28, 2006

(54) METHOD FOR TUMOR TREATMENT USING INFUSION OF XENOGENEIC CELLS TO INDUCE HYPERACUTE REJECTION AND INNOCENT BYSTANDER EFFECT

(75) Inventors: Charles J. Link, Jr., Clive, IA (US); Tatiana Seregina, West Des Moines, IA (US)

(73) Assignee: Human Gene Therapy Research Institute, Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/589,255

(22) Filed: Jun. 7, 2000

Related U.S. Application Data (60) Provisional application No. 60/138,038, filed on Jun. 8, 1999.

(51) Int. Cl.
*A61K 48/00* (2006.01)
*C12N 5/00* (2006.01)
*C12N 15/00* (2006.01)
*C12N 15/74* (2006.01)

(52) U.S. Cl. .................. 424/93.21; 424/93.1; 424/93.2; 424/277.1; 514/44; 435/320.1; 435/325

(58) Field of Classification Search ............... 424/93.1, 424/93.2, 93.21, 277.1; 514/44; 435/320, 435/325
See application file for complete search history.

(56) References Cited

U.S. PATENT DOCUMENTS 5,869,035 A * 2/1999 Link, Jr. et al. ........... 424/93.7

6,045,789 A * 4/2000 Culver et al. ............ 424/93.21

OTHER PUBLICATIONS

Verma et.al.; Gene therapy- promises, problems and prospects, 1997, Nature, vol. 389: 239-242.*
Orkin et.al.; Report and Recommendations of the Panel to Assess the NIH Investment in Research on Gene Therapy, 1995.*
Ross et. al.; Gene Therapy in the United States: A Five-Year Status Report, 1996, Human Gene Therapy 7: 1781-1790.*
Klatzmann et.al.; A Phase I/II Dose-Escalation Study of Herpes Simplex Virus Type I Thymidine Kinase "Suicide" Gene Therapy for Metastatic Melanoma, 1998, Human Gene Therapy 9: 2585-2594.*
Appleton et.al.; Gene Therapy of Cancer V, 1996, Cancer Gene Therapy vol. 3, No. 6.*
Link, Jr. et.al.; Eliciting Hyperacute Xenograft Response to Treat Human Cancer: . . . Gene Therapy, 1998, Anticancer Research 18: 2301-2308.*
Link et al. (1996) Human Gene Ther., vol. 7, 1161-1179.*
Long et al. (1998) Human Gene Therapy, vol. 9, 1165-1172.*

* cited by examiner

*Primary Examiner*—Anne M. Wehbé
(74) *Attorney, Agent, or Firm*—McKee, Voorhees & Sease, P.L.C.

(57) ABSTRACT

A method for treating tumors. Through infusion or xenotransplantation of xenogeneic cells, such as infusion of murine cells into the peritoneal cavity of humans, a hyperacute rejection response to the cells is induced. This in turn creates a bystander effect to the tumor. This effect creates tumor regression. This treatment can be used alone or in conjunction with gene therapy or chemotherapy treatments.

8 Claims, 6 Drawing Sheets

SEQUENCE LISTING

<160> NUMBER OF SEQ ID NOS: 4

<210> SEQ ID NO 1
<211> LENGTH: 19
<212> TYPE: DNA
<213> ORGANISM: retroviral provirus

<400> SEQUENCE: 1
acctggagag tcaccaacc                                              19

<210> SEQ ID NO 2
<211> LENGTH: 20
<212> TYPE: DNA
<213> ORGANISM: retroviral provirus

<400> SEQUENCE: 2
tactttggag aggtcgtagc                                             20

<210> SEQ ID NO 3
<211> LENGTH: 21
<212> TYPE: DNA
<213> ORGANISM: retroviral provirus

<400> SEQUENCE: 3
tatagacggt cctcacggga t                                           21

<210> SEQ ID NO 4

```
<211> LENGTH: 20
<212> TYPE: DNA
<213> ORGANISM: retroviral provirus

<400> SEQUENCE: 4
tcatgctgcc cataaggtat                                              20
```

METHOD FOR TUMOR TREATMENT USING INFUSION OF XENOGENEIC CELLS TO INDUCE HYPERACUTE REJECTION AND INNOCENT BYSTANDER EFFECT

CROSS-REFERENCE TO RELATED APPLICATION

This application claims the benefit of U.S. Provisional Patent Application No. 60/138,038 filed Jun. 8, 1999, which is hereby incorporated by reference.

BACKGROUND OF THE INVENTION

Ovarian carcinoma is the most common cause of death from a gynecological malignancy in the United States. Over ⅔ of the patients have advanced stage disease at presentation for which systemic chemotherapy is indicated after surgical debulking. Standard therapy consists of cisplatin or carboplatin with paclitaxel, and excellent response rates are observed; however, recurrence is common, and the majority of patients still die of disease progression. Ovarian cancer has a fairly unique natural history in humans. Even patients with advanced stages of the disease often have their disease confined to their abdomen for extended periods of time. The disease often stays localized to the abdomen and presents great difficulty for the patient by obstruction of the intestines or ureters. This natural history makes the possibility of locally-targeted therapy realistic. As a result, intraperitoneal therapies have been developed for the local administration of chemotherapeutic agents into the peritoneal cavity.

Gene therapy is among the experimental strategies for patients with cancer who have failed standard therapy. Despite more than 100 gene therapy trials, evidence of success is very limited. Roth, J. A., Cristiano, R. J., Roth, J. A. & Cristiano, R. J., Gene therapy for cancer: what have we done and where are we going? J. Natl. Cancer Inst. 89(1), 21–39 (1997). One strategy which has been explored for treating cancer is the artificial creation of differences between normal and neoplastic cells through prophylactic use of gene insertion techniques. In other words, manufacturing biochemical differences which can be exploited to systematically and specifically target neoplastic cells for destruction. Gene insertion protocols are used to artificially manufacture biochemical differences in target tumor cells which are then exploited to selectively kill these cells. One system which has received much attention to date is the Herpes Simplex Virus Ganciclovir System.

Transformation of tumor cells with the gene encoding Herpes Simplex Virus thymidine kinase (HSVtk) and subsequent treatment with anti-viral agents such as ganciclovir (GCV) has been previously accomplished and has proven to be operable in vivo in animals and humans. See Gene Therapy for the Treatment of Recurrent Pediatric Malignant Astrocytomas With In Vivo Tumor Transduction With Herpes Simplex Thymidine Kinase Gene/Ganciclovir System, Raffel, C. et al., Human Gene Therapy 5(7), p. 863–90, July 1994. The HSVtk gene is negative selectable marker or "suicide" gene of which most investigators in the field are well aware and versed in how the system is supposed to function. HSVtk sensitizes transduced tumor cells to GCV. Moolten, F. L., Tumor chemosensitivity conferred by inserted herpes thymidine kinase genes: Paradigm for a prospective cancer control strategy Cancer Res. 46, 5276–5281 (1986); Moolten, F. L. & Wells, J. M., Curability of tumors bearing herpes thymidine kinase genes transferred by retroviral vectors J. Nat. Cancer Inst. 82, 297–300 (1990); Moolten, F. L., Wells, J. M., Heyman, R. A. & Evans, R. M., Lymphoma regression induced by ganciclovir in mice bearing a herpes thymidine kinase transgene Human Gene Ther. 1, 125–134 (1990); Plautz, G., Nabel, E. G. & Nabel, G. J., Selective elimination of recombinant genes in vivo with a suicide retroviral vector New Biologist 3(7), 709–715 (1991). GCV is phosphorylated by HSVtk resulting in a monophosphate that cellular kinases convert to GCV-triphosphate which inhibits DNA replication and causes cell death. An interesting in vitro and in vivo observation with HSVtk is that only a portion of tumor cells need to be transduced with this gene to induce complete tumor destruction. This metabolic cooperation is a form of "bystander effect" and is due in large part to the transfer of phosphorylated GCV between cells through gap junctions. Moolten, F. L., Tumor chemosensitivity conferred by inserted herpes thymidine kinase genes: Paradigm for a prospective cancer control strategy Cancer Res. 46, 5276–5281 (1986); Culver, K. W., Ram, Z., Walbridge, S., Ishii, H., Oldfield, E. H., and Blaese, R. M. In vivo gene transfer with retroviral vector-producer cells for treatment of experimental brain tumors Science 256, 1550–1552 (1992); Nielsen, C. S., Moorman, D. W., Levy, J. P. & Link, C. J., Jr., Herpes simplex thymidine kinase gene transfer is required for complete regression of murine colon adenocarcinoma Am. Surg. 63(7), 617–620 (1997); Bi, W. L., Parysek, L. M., Warnick, R. & Stambrook, P. J., In vitro evidence that metabolic cooperation is responsible for the bystander effect observed with HSVtk retroviral gene therapy Hum. Gene Ther. 4, 725–731 (1993); Freeman, S. M., Abboud, C. N., Whartenby, K. A., Packman, C. H., Koeplin, D. S., Moolten, F. L., and Abraham, G. N. The bystander effect: tumor regression when a fraction of the tumor mass is genetically modified Cancer Res. 53, 5274–5283 (1993); Ishii-Morita, H., Agbaria, R., Mullen, C. A., Hirano, H., Koeplin, D. A., Ram, Z., Oldfield, E. H., Johns, D. G., and Blaese, R. M. Mechanism of 'bystander effect' killing in the herpes simplex thymidine kinase gene therapy model of cancer treatment Gene Ther. 4(3), 244–51 (1997); Link, C. J., Jr., Kolb, E. M. & Muldoon, R. R., Preliminary in vitro efficacy and toxicities studies of the herpes simplex thymidine kinase gene system for the treatment of breast cancer Hybridoma 14(2), 143–7 (1995); Samejima, Y. & Meruelo, D., 'Bystander killing' induces apoptosis and is inhibited by forskolin Gene Therapy 2, 50–58 (1995); Vrionis, F. D., Wu, J. K, Qi, P., Waltzman, M., Cherington, V., and Spray, D. C. The bystander effect exerted by tumor cells expressing the herpes simplex virus thymidine kinase (HSVtk) gene is dependent on connexin expression and cell communication via gap junctions Gene Ther. 4(6), 577–85 (1997). The implantation of vector producer cells (VPC) to deliver genes, such as the HSVtk gene, into tumor cells was first demonstrated in a brain tumor model by engrafting lacZ VPC into rodents with C6 glioma tumors. Short, M. P., Choi, B. C., Lee, J. K., Malick, A., Breakefield, X. O., and Martuza, R. L. Gene delivery to glioma cells in rat brain by grafting of a retrovirus packaging cell line J. Neurosci. Res. 27, 427–439 (1990). In these reported animal tumor models, all of the rodents are αgal+. Since these were αgal+ models, hyperacute rejection is not contributing to the observed responses with the HSVtk system. A human, however, is different.

Three prior human trials of murine HSVtk VPC have been reported; two for treatment of brain tumors and one for melanoma. Results from the first clinical trial conducted at the NCI using murine VPC xenografts were recently reported in *Nature Medicine*. Ram, Z., Culver, K. W., Oshiro, E. M., Viola, J., DeVroom, H. L., Otto, E., Long, Z., Chiang, Y., McGarrity, G. J., Muul, L. M., Katz, D., Blaese, R. M., and Oldfield, E. H. Therapy of malignant brain tumors by intratumoral implantation of retroviral vector-producing cells Nature Med. 3, 1354–1361 (1997). This trial used multiple stereotaxic injections to introduce murine HSVtk VPC into the enhancing portion of brain tumors. Antitumor activity was observed in selected local tumor deposits in 5 of 19 tumors injected in 13 patients. Ram, Z. et al., Nature Med. 3, 1354–1361 (1997). It is important to note that very limited (minimal) gene transfer was observed. The sterotaxic injections required multiple needle passages to try to distribute the VPC throughout the tumors resulting in severe hemorrhage that required surgery in 2 patients and MRI-visible bleeding in most of the other tumors. The authors theorized that the observed responses were secondary to the cell-to-cell transfer of phosphorylated GCV as "the major mechanism" of the bystander effect and concluded that "non-immune bystander mechanisms were critical." Ram, Z. et al., Nature Med. 3, 1354–1361 (1997). They further stated that the observed responses were "probably not a result of immune mechanisms." In light of data presented in this application and data from others demonstrating rapid destruction of murine VPC by human serum, these conclusions are unwarranted. Rollins, S. A., Birks, C. W., Setter, E., Squinto, S. P. & Rother, R. P., Retroviral vector producer cell killing in human serum is mediated by natural antibody and complement: Strategies for evading the humoral immune response Human Gene Therapy 7, 619–626 (1996); Link, C. J., Levy, J. P., Seregina, T., Atchinson, R. & Moorman, D., in Cancer Gene Therapy (eds Mazarakis, H. & Swart, S. J.) 135–152 (IBC Library Series, London, United Kingdom, 1997). We suggest that the contrast enhancement reported along the needle tracts of VPC injections, as well as the transient volume increase of the tumors immediately after injection, was more likely to be the result of antibodies (Ab) and complement-mediated hyperacute rejection against the murine cells. Of note, the authors did report an increase in VPC binding Ab that peaked 21-142 days after VPC injection; these Ab may represent anti-αgal Ab. Ram, Z. et al., Nature Med. 3, 1354–1361 (1997). Other groups have shown that anti-pig Ab present in human serum are predominantly anti-αgal IgM Ab. Vaughan, H. A., McKenzie, I. F. & Sandrin, M. S. Biochemical studies of pig xenoantigens detected by naturally occurring human antibodies and the galactose alpha(1,3)galactose reactive lectin Transplantation 59(1), 102–9 (1995). The time frame of Ab titer increase is similar to that reported for diabetic patients transplanted with porcine islet xenografts and with our results with murine VPC intraperitoneal infusions discussed below. Galili, U., Tibell, A., Samuelsson, B., Rydberg, L. & Groth, C. G. Increased anti-Gal activity in diabetic patients transplanted with fetal porcine islet cell clusters Transplantation 59 (11), 1549–56 (1995).

A second brain tumor trial was recently reported by Klaztmann and colleagues. Klatzman, D., Valery, C. A., Bensimon, G., Marro, B., Boyer, O., Mokhtari, K., Diquet, B., Salzman, J.-L., Philippon, J., and Glioblastoma, S.G.o.G.T.f. A phase I/II dose escalation study of Herpes simplex virus type 1 thymidine kinase "suicide" gene therapy for recurrent glioblastoma Human Gene Ther. 9, 2595–2604 (1998). M11 murine VPC producing HSVtk retroviral vector were injected into the tumor margin after surgical debulking. Seven days later, patients were treated with GCV. Twelve patients were treated without side effects that the physicians attributed to the VPC or GCV. The authors claimed that the observed responses were secondary to gene therapy. One patient was still alive without evidence of progression by MRI at 2.8 years after the procedure. Eleven of twelve patients had died; nine from tumor progression, one from head trauma, and one from pulmonary embolus. To relate these observations to the gene therapy, the authors suggested several indirect lines of evidence. First, M11 cells could be recovered from surgical drain fluids 24 hours after cell injections. However, M11 VPC were recovered from only 3 out of 6 patients even at this short time point. Furthermore, no viable cells were recovered at later time points. Again, neurosurgical procedures with local tumor resections are operations with active bleeding and oozing into the tumor bed where the cells were injected. In fact, a blood-brain barrier that has been quoted by a number of groups to protect murine VPC (Ram, Z., J. Neurosurg. 79, 400–7 (1993)) is mechanically destroyed by the scalpel during major surgical debulking. Thus, M11 cells were most likely quickly lysed by the presence of human serum. The ability to recover a few viable M11 cells from the surgical drain 1 day after up to $9.8 \times 10^6$ cells/cm$^2$ were injected is not compelling evidence that gene transfer is accounting for these observations. The second indirect evidence proposed was that GCV plasma levels were in a therapeutic range to kill HSVtk expressing cells. It is not understood how the presence of an adequate GCV level provides evidence of causation without HSVtk gene transfer data. No gene transfer into glioblastoma cells was reported. The imaging and pathologic data from this trial does suggest that patients who did not demonstrate MRI progression at 4 months after VPC injection do show some efficacy; however, the relationship between these observed responses and HSVtk and GCV is highly speculative.

One other study was performed on melanoma patients with non-CNS malignancy. Klatzman, D. et al., Human Gene Ther. 9, 2585–2594 (1998). Eight patients were treated by the direct injection of murine M11 packaging cells that produced HSVtk vector. The total cell dose ranged from $8 \times 10^7$ to $12.5 \times 10^8$ cells that were directly injected into tumors. Inflammatory reactions were common immediately after these xenogeneic VPC were injected. A rapid increase in tumor size was noted that peaked 24 hours later. The investigators attributed these effects to known pre-existing antibodies against xenogeneic antigens present on murine cells. This suggestion supports our findings. The very limited anti-tumor effects were some areas of local necrosis noted on biopsy samples. The lack of significant efficacy was attributed to poor gene transfer (<1% or none detected by PCR). Side effects of therapy consisted chiefly of local inflammatory reactions or fever when multiple injections were administered. This group suggested that murine VPC survival was enhanced by using intravenous immunoglobulin to delay xenogeneic hyperacute rejection. Gautreau, C., Kojima, T., Woimant, G., Cardoso, J., Devilier, P., and Houssin, D. Use of intravenous immunoglobulin to delay xenogeneic hyperacute rejection Transplantation 9, 903–907 (1995).

Hyperacute rejection of xenografts has been previously explored due to the great interest in using animals as a source of organs or tissues for humans. Strong immunological barriers to xenotransplants can destroy a transplanted solid organ within minutes, a process termed hyperacute rejection. This hyperacute rejection model of xenograft survival is typically a vascularized xenograft directly exposed to blood serum. Pruitt, S. K., Kirk, A. D., Bollinger, R. R., Marsh, J., Henry, C., Collins, B. H., Levin, J. L., Mault, J. R., Heinle, J. S., Ibrahim, S., Rudolph, A. R., Baldwin, I., William, M., and Sanfilippo, F. The effect of soluble complement receptor type 1 on hyperacute rejection of porcine xenografts Transplantation 57, 363–370 (1994). Research has demonstrated that hyperacute rejection with porcine xenografts transplanted into baboons occurs secondary to porcine α(1,3)galactosyltransferase [α(1,3)GT] gene expression and α(1,3)galactosyl epitopes (αgal) presentation. Pruitt, S. K. et al., Transplantation 57, 363–370 (1994); Platt, J. L., Vercellotti, G. M., Dalmasso, A. P., Matas, A. J., Bolman, R. M., Najarian, J. S., and Bach, F. H. transplantation of discordant xenografts: a review of progress Immunol. Today 17, 450–457 (1990). The enzyme α(1,3)GT is expressed in all mammalian species including *Mus musculus*, but not in Old World primates, apes, or humans. Galili, U. Shohet, S. B., Kobrin, E., Stults, C. L. & Macher, B. A., Man, apes, and Old World monkeys differ from other mammals in the expression of alpha-galactosyl epitopes on nucleated cells J. Biol. Chem. 263(33), 17755–62 (1988). The α(1,3)GT gene is not active in humans due to the presence of two base pair frameshift mutations. Larsen, R. D., Rivera-Marrero, C. A., Ernst, L. K., Cummings, R. D. & Lowe, J. B., Frameshift and nonsense mutations in a human genomic sequence homologous to a murine UDP-Gal:beta-D-Gal(1,4)-D-GlcNAc alpha(1,3)-galactosyltransferase cDNA J. Biol. Chem. 265(12), 7055–61 (1990). α(1,3)GT catalyzes the transfer of galactose from uridine diphosphate galactose (UDP-Gal) to the N-acetyl-lactosamine acceptors on carbohydrate side chains in a specific α(1,3)linkage on glycoproteins or glycolipids (Galβ1→4GlcNAc-R).

Galβ1→4GlcNAc-R+UDP-Gal→Galα1→3Galβ1→4GlcNAc-R Anti-αgal Ab present in the human serum can recognize this epitope. Galili, U. Shohet, S. B., Kobrin, E., Stults, C. L. & Macher, B. A., J. Biol. Chem. 263, 17755–62 (1988). In fact, pre-existing human Ab against αgal represent almost 1% of total human Ab (Galili, U., Evolution and pathophysiology of the human natural anti-y-galactosyl IgG (anti-Gal) antibody Springer Semin. Immunopathol. 15, 155–171 (1993)) and are the basis for complement-mediated hyperacute rejection. Sandrin, M. S., Vaughan, H. A., Dabkowski, P. L. & McKenzie, I. F. Anti-pig IgM antibodies in human serum react predominantly with Gal(alpha 1–3)Gal epitopes Proc. Natl. Acad. Sci. U.S.A. 90(23), 11391–5 (1993). Human anti-αgal Ab are thought to arise in response to αgal structures on the surface of normal GI flora. The translocation of viable bacteria from the enteric lumen to the mesenteric lymph nodes is thought to stimulate the host immune response. Neonatal humans and baboons compared to their respective adults have very low titers of anti-αgal IgM Ab, the isotype most effective in binding complement. Xu, H., Edwards, N. M., Dong, X. & Michler, R. E. Age-related development of human preformed anti-porcine endothelial cell xenoantibody J. Thorac. Cardiovasc. Surg. 15, 1023 (1995); Minanov, O. P., Itescu, S., Neethling, F. A., Morgenthau, A. S., Kwiatkowski, P., and Cooper, D. K. Anti-gal IgG antibodies in sera of newborn humans and baboons and its significance pig xenotransplantation Transplantation 63, 182 (1997). Neonatal circulating xenoreactive Ab are of the IgG isotype, presumably attained by placental transfer of maternal IgG. Xu, H., Edwards, N. M., Dong, X. & Michler, R. E., J. Thorac. Cardiovasc. Surg. 15, 1023 (1995); Minanov, O. P. et al., Transplantation 63, 182 (1997); Galili, U., Springer Semin. Immunopathol. 15, 155 (1993). Since newborn gut is sterile, there is a time period in which newborn primates are not exposed to bacterial αgal moieties and, thus, lack de novo Ab directed against these epitopes.

Murine vector producing cells implanted into humans is another type of xenograft. It has been demonstrated that murine retroviral VPC and the viral vectors they produce express αgal and, therefore, are lysed by Ab and complement within 30 minutes after being exposed to human serum. Link, C. J., Levy, J. P., Seregina, T., Atchinson, R. & Moorman, D., Cancer Gene Therapy (eds Mazarakis, H. & Swart, S. J.) 135–152 (IBC Library Series, London, United Kingdom, 1997); Welsh, R. M., Cooper, N. R., Jensen, F. C. & Oldstone, M. B., Human serum lyses RNA tumor viruses Nature 257, 612–614 (1975); Rother, R. P., Fodor, W. L., Springhorn, J. P., Birks, C. W., Setter, E., Sandrin, M. S., Squinto, S. P., and Rollins, S. A. A novel mechanism of retrovirus inactivation in human serum mediated by anti-alpha-galactosyl natural antibody J. Exp. Med. 182(5), 1345–55 (1995). The effect of this serum inactivation on VPC and retroviruses is due to αgal expression on the cells. Link, C. J., Levy, J. P., Seregina, T., Atchinson, R. & Moorman, D., Cancer Gene Therapy (eds Mazarakis, H. & Swart, S. J.) 135–152 (IBC Library Series, London, United Kingdom, 1997); Rother, R. P. et al., J. Exp. Med. 182, 1345–55 (1995); Rother, R. P., Squinto, S. P., Mason, J. M. & Rollins, S. A., Protection of retroviral vector particles in human blood through complement inhibition Hum. Gene Ther. 6(4), 429–35 (1995).

Viral vectors can efficiently transduce human tumor cells with anti-tumor therapeutic genes. As part of a study of blocking retroviral destruction by using human packaging cells, the transfer of the porcine α(1,3)GT to human fibroblasts was shown to result in sensitivity to Ab and complement destruction. Collins, M. K., Takeuchi, Y., Cosset, F. L., Tailor, C. & Weiss, R. A. Development of recombinant retroviruses suitable for in vivo gene delivery Cold Spring Harbor Meeting: Gene Therapy September 1994, 97 (1994). We have found that the retroviral transduction of human tumor cells with the α(1,3)GT gene resulted in its expression. These human cells displayed αgal and became sensitive to human serum. In this project, murine VPC are employed to deliver retroviral vector to intraperitoneal ovarian tumors. We are interested in the biology of glycosylation and the immunologic effect of αgal epitopes. Therefore, the project goal is to further understand mechanisms of hyperacute rejection. Hyperacute rejection may cause a strong intraperitoneal inflammatory response, that through an innocent bystander mechanism, destroys ovarian cancer cells. The process of local tumor destruction might result in the disruption of tumor anergy. This has been a common strategy in gene modification trials. Previous attempts of immunotherapy have mainly employed single cytokine molecules (e.g., IL-2, GM-CSF) (Golumbek, P. T., Lazenby, A. J., Levitskky, H. I., Jaffee, L. M., Karasuyama, H., Baker, M., and Pardoll, D. M. Treatment of established renal cancer by tumor cells engineered to secrete interleukin-4 Science 254, 713716 (1991); Dranoff, G., Jaffee, E., Lazenby, A., Golumbek, P., Levitsky, H., Brose, K., Jackson, V., Hamada, H., Pardoll, D., and Mulligan, R. Vaccination with irradiated tumor cells engineered to secrete murine GM-CSF stimulates potent, specific, and long lasting anti-tumor immunity Proc. Natl. Acad. Sci. (USA) 90, 3539–3543 (1993); Fearon, E. R., Pardoll, D. M., Itaya, T., Golumbek, P., Levitsky, H. I., Simons, J. W., Karasuyama, H., Vogelstein, B., and Frost, P. Interleukin-2 production by tumor cells bypasses T helper function in the generation of an antitumor response Cell 60, 397–403 (1990)) or single rejection antigens (e.g., HLA B7, melanoma specific tumor antigen). Nabel, G. J., Nabel, E., Yang, Z., Fox, B. A., Plautz, G. E., Gao, X., Huang, L., Shu, S., Gordon, D., and Chang, A. E. Direct gene transfer with DNA-liposome complexes in melanoma: Expression, biologic activity, and lack of toxicity in humans Proc. Natl.

Acad. Sci. (USA) 90, 11307– 11311 (1993); Reeves, M. E., Royal, R. E., Lam, J. S., Rosenberg, S. A. & Hwu, P. Retroviral transduction of human dendritic cells with a tumor-associated antigen gene Cancer Res. 56(24), 5672–7 (1996).

Since anti-tumor gene therapy requires highly efficient gene transfer and expression of therapeutic genes (Roth, J. A., Cristiano, R. J., Roth, J. A. & Cristiano, R. J. Gene therapy for cancer: what we have done and where are we going? J. Natl. Cancer Inst. 89(1), 21–39 (1997)) and the Goldie-Coldman hypothesis predicts that spontaneous mutations in cancer cells provide resistance to chemotherapy and that therapeutic failures are directly related to tumor burden (Goldie, J. H. & Coldman, A. J. A mathematic model for relating the drug sensitivity of tumors to their spontaneous mutation rate Cancer Treat. Rep. 63(11–12), 1727–33 (1979)), multiple, independent therapeutic targets need to be attacked for success. The predicted tumor resistance will likely extend to gene therapy as well; for example, our group has demonstrated that resistance to HSVtk gene and GCV killing is common in tumor cells. Seregina, T., Levy, J. & Link, C. in Fourth International Conference on the Gene Therapy of Cancer Vol. 2 (eds Sobol, R. E. & Royston, I.) A332 (Appleton & Lange, San Diego, Calif., 1995). In the future, gene delivery methods that transfer multiple therapeutic genes in concert or genes with multiple mechanisms of action will dominate approaches for cancer treatment.

All references cited throughout this application are hereby incorporated by reference.

Based on the foregoing, it is desirable that a less complicated system without use of vectors be available. Using VPC could be eliminated using the present invention, thus, taking away the additional risk to the patient of using viral vectors. The present invention is able to create antitumor responses without the need for gene transfection and addition of a prodrug.

SUMMARY OF THE INVENTION

An object of the invention is a method of tumor treatment.

Another object of the invention is a method for treating cancer by activation of hyperacute rejection in or near the tumor(s).

A further object of the invention is a method for inducing an immune reaction to attack tumor cells.

These and other objects, features, and advantages will become apparent after review of the following description and claims of the invention which follow.

The present invention induces hyperacute rejection in and/or in the vicinity of a tumor by xenotransplantation/infusion of xenogeneic cells. The xenogeneic cells activate the hyperacute rejection response to themselves and induce an immune reaction in which tumor cells are destroyed. One mechanism of tumor destruction may be by an innocent bystander effect.

It may be possible to add to this effect by infusing cells which transfect the tumor cells with a gene that the immune system will respond to, for example, one which creates α(1,3)galactosyl epitopes in a human system (see, e.g., U.S. Pat. No. 5,869,035, hereby incorporated by reference).

Additionally, subsequent treatment with a prodrug which is activated by the gene which was introduced may be added to the therapy. For example, if the HSVtk gene is introduced, ganciclovir may be used (see, e.g., U.S. Pat. No. 5,631,236, hereby incorporated by reference).

BRIEF DESCRIPTION OF THE DRAWINGS

FIG. 1 shows gels of PCR analysis of patient 4 who received 680 million murine LTKOSN.1 vector producer cells (VPC) into the peritoneal cavity. TOP: PCR amplification for the HSVtk gene. Positive controls: LTKOSN plasmid only (10 fg), A375 human melanoma cells mixed with 0.1%, 0.01%, 0% A375 cells transduced with LTKOSN vector; intraperitoneal tumor biopsy from day −1 (before VPC infusion) and 14 days after infusion (before GCV); peritoneal washings obtained at day −1 before and days 3 to 35 after VPC infusion. HSVtk gene sequence is detected in the day 14 tumor biopsy and on days 3 and 7 after VPC infusion. BOTTOM: PCR amplification for the viral env gene. Positive controls: pPAM plasmid containing the viral env gene (10 fg), 0.1% or 0.01% LTKOSN.1 VPC; intraperitoneal tumor biopsy from day −1 and 14; peritoneal washings at day −1, 3, 7, 14 and 35 after VPC infusion. The env gene sequence is detected in the day 3 and 7 peritoneal washings, but not from the tumor biopsy. Therefore, VPC are lost from the abdominal cavity after day 7.

DETAILED DESCRIPTION OF THE PREFERRED EMBODIMENT

It has been found that there is an anti-tumor response in women with recurrent ovarian cancer treated with LTKOSN.1 murine VPC and GCV due to the induced immune effect mediated by the activation of hyperacute rejection against non-primate cells that are infused to produce murine retroviral vectors in situ which is prior to any effect by the transfection of the cells or activation of the GCV.

Murine cells express a surface glycosylation pattern that is not present on human cells. The murine α(1,3)galactosyltransferase [α(1,3)GT] enzyme adds α(1,3)galactosyl epitopes (αgal) onto glycoproteins and glycolipids. Pre-existing human antibody can bind these epitopes and fix complement resulting in the direct lysis of the murine cells. Our data suggests that an innocent bystander effect then occurs which induces the destruction of adjacent cancer cells and possibly stimulates anti-tumor immunity. Though it is believed the bystander effect is responsible for destruction of the tumor cells, a different or several mechanisms may be responsible.

The present inventions seeks to shift the current understanding of published trials stating that HSVtk and ganciclovir (GCV) gene therapy is efficacious for the treatment of solid tumors in adults. These trials were designed with the idea that murine VPC xenografts would provide the production of retroviral vectors within solid tumors and efficiently transfer the HSVtk gene. This gene transfer was then expected to sensitize solid tumors to GCV. Furthermore, a bystander effect caused by metabolic cooperation was to enhance the effect, so that if only a small portion of the tumor was transduced with HSVtk, then the entire tumor could be destroyed. In cell culture and animal models of HSVtk and GCV therapy, 10–20% of the tumor needed to express the HSVtk gene to obtain complete response. Moolten, F. L., Cancer Res. 46, 5276–5281 (1986); Culver, K. W. et al., Science 256, 1550–1552 (1992); Link, C. J., Kolb, E. & Muldoon, R., Hybridoma 14, 143–147 (1995). The implantation of VPC is superior to implanting HSVtk pre-transduced cells alone to increase the delivery of the HSVtk gene. However, in animal models, this approach is often not successful even when 50% of the cells are pretransduced with HSVtk for a variety of human tumor xenografts (Link, unpublished observations). In a preclinical model of intraperitoneal colon adenocarcinoma treated with LTKOSN VPC, a 50% transduction frequency was required to cure 50% of the animals of syngeneic MC38 tumor grafts. Link, C. J., Kolb, E. & Muldoon, R., Hybridoma. 14, 143–147 (1995). Therefore, high level gene transfer is required in these model systems, and it is very unlikely that the conditions for in vivo gene transfer in humans would be more favorable. Specifically, these trials have made claims that are overly simplistic and presume an effect of HSVtk gene and GCV on tumors. These agents have now been expanded into larger trials in the United States and abroad. Further scientific understanding of the basic human immune response to these murine vector producer cells should aid in the further development of VPC technology and provide insight into this potentially important approach to cancer treatment.

A Phase I trial of 10 patients with recurrent ovarian or fallopian tube cancers was conducted using the xenotransplantation of murine retroviral LTKOSN.1 VPC for in vivo transfer of the HSVtk gene. All patients had failed prior therapy with paclitaxel and either cisplatin or carboplatin. LTKOSN.1 VPC were infused into the peritoneal cavity in doses from $1\times10^6$ to $1\times10^8$ cell/kg. After 4 weeks, patients were treated with GCV for 2 weeks. Viable VPC were recovered from peritoneal washes on day +3 and/or day +7 after infusion at the two highest dose levels. The recovered VPC were still able to produce high titer LTKOSN retroviral vector. VPC were detectable by PCR up to day +7, but at day +14 none were detected. Tumor tissue obtained on day +14 prior to first GCV injection were positive for the HSVtk gene by PCR. Four of ten evaluable patients demonstrated some evidence of anti tumor response. One patient had a complete resolution of a 2 cm mass on CT scan and a 70% reduction of CA125. Of the remaining 3, first patient had a partial, second patient a minor, and the third patient showed a mixed response to the treatment. The patient with the mixed response demonstrated significant resolution of malignant ascites prior to GCV infusion, but developed a malignant pleural effusion. Quantitative PCR analysis demonstrated less than 1% gene transfer into intraperitoneal tumor biopsies prior to GCV administration. All patients were treated as outpatients.

It is surprising that anti-tumor responses were observed although only low level gene transfer was noted. These data suggest the process of hyperacute rejection associated with the administration of murine VPC has an adverse effect on the intraperitoneal tumor.

Since it is believed that the gene transfer was not necessary to the anti-tumor reaction, it is believed that any xenogeneic cells which will activate the hyperacute rejection will be effective in the invention. One of ordinary skill in the art would be able to determine which cells other than murine cells which will be safe and effective. There are many commercial and academic sources of cell lines. Additionally, one of ordinary skill would be able to develop cells lines to use in the present invention.

The Examples show that the xenogeneic cells were infused into the peritoneal cavity in the vicinity of the tumor using a catheter. One of ordinary skill would be able to determine other methods of presenting the xenogeneic cells to the body in order to induce the hyperacute rejection and bystander effect.

The dose levels of xenogeneic cells that have been used are shown in the Examples. One of ordinary skill would be able to determine a dose level appropriate for the tumor and the patient which is both safe and effective.

The prior art method of gene expression and activation of an added prodrug may be effective used concurrently with the treatment of the present invention (hyperacute rejection/bystander effect), this gene therapy/prodrug method may be used as an add-on therapy. Additionally, since it appears that the physiology of the tumor changes after induction of the hyperacute rejection and the bystander effect, chemotherapy appears to be effective after the treatment of the present invention where the chemotherapy was achieving little, if any, results prior to this new treatment. One of ordinary skill would be able to determine additional treatments which will work prior to, in conjunction with, or subsequent to the present treatment.

The vector present in the VPC that was used in the present invention was LTKOSN. LTKOSN is a retroviral vector derived from the Moloney murine leukemia virus (Mo-MLV). The vector LTKOSN contains a Herpes Simplex type I thymidine kinase (HSVtk) gene cDNA that is transcribed from the viral long terminal repeat (LTR) and a bacterial neomycin resistance ($neo^r$) gene transcribed from an internal SV40 (simian virus 40) early promoter (LTR-HSVtk-SV-$neo^r$-LTR) in the LXSN backbone. This vector has been modified for increased safety by alteration of the gag start codon to a stop codon, and by elimination of viral sequences to minimize the potential for the development of replication-competent virus from producer cells which contain the vector.

The present invention was used to treat ovarian and fallopian cancer which are solid tumors. One of ordinary skill would be able to determine other tumors which will respond to the treatment of the present invention.

The data from the Phase I trial of the present approach did not support the published conclusions of researchers (e.g., Ram, Z. et al., Nature Med. 3 1354–1361 (1997); Klatzman, D. et al., Human Gene Ther. 9, 2585–2594 (1998)). The current trial was designed to determine if antitumor responses observed in earlier trials, often attributed by other investigators to HSVtk enzyme activation of GCV, is correct. The current paradigm theorized that HSVtk gene activation of GCV leads to a bystander effect that accounts for observed antitumor responses. The results of this investigation may overturn the current paradigm accepted by investigators in molecular medicine. This finding leads to better scientific and clinical investigations if VPC is the delivery vehicle. The current investigation also provides insight into novel antitumor mechanism (hyperacute rejection) and might be further developed and exploited to benefit cancer patients.

EXAMPLES

Example 1

Destruction of Murine Cells by Human Serum and Peritoneal Fluid

The initial interest in hyperacute rejection resulted from studies of destruction of murine vector producer cells (VPC) by peritoneal fluid. VPC have been proposed for in vivo gene delivery as a potential improvement over retroviral particles alone to increase the transduction efficiency in tumor models. Short, M. P., Choi, B. C., Lee, J. K., Malick, A., Breakefield, X. O., and Martuza, R. L., Gene delivery to glioma cells in rat brain by grafting of a retrovirus packaging cell line J. Neurosci. Res. 27, 427–439 (1990). The human serum mediated destruction of murine VPC was immediate. The results indicated that substantial VPC killing occurred after their exposure to peritoneal fluid. It was demonstrated that heparin, enoxaparin, or sCR1 could specifically block lysis of murine cells by human serum. Link, C. J., Levy, J. P., Seregina, T., Atchinson, R. & Moorman, D., Cancer Gene Therapy (eds Mazarakis, H. & Swart, S. J.) 135–152 (IBC Library Series, London, United Kingdom, 1997). sCR1 is a soluble form of complement receptor 1 that binds activated complement and prevents the attack complex from damaging the cell membrane.

Example 2

Phase I Clinical Trial of LTKOSN.1 VPC for Women with Recurrent Ovarian Cancer A Phase I clinical trial was completed with 10 patients with recurrent ovarian or fallopian tube cancer. This study was conducted using the xenotransplantation of murine retroviral LTKOSN.1 VPC for in vivo transfer of the HSVtk gene. All patients had failed prior therapy with paclitaxel and either cisplatin or carboplatin. All patients were treated as outpatients. LTKOSN.1 VPC were infused intraperitoneally with doses from $1\times10^6$ to $1\times10^8$ cell/kg. After 2 weeks, patients were treated for two weeks with ganciclovir (GCV). The data is detailed in Tables 1 and 2.

TABLE 1

Clinical Outcome in Ovarian Cancer Patients Treated with LTKOSN.1 VPC.

| Patient | Age/Stage | Tumor | Dose level | Dose (VPC) | Signs and symptoms | Gene transfer observed | Result | Comments |
|---|---|---|---|---|---|---|---|---|
| 1 | 64 IIIC | Ovarian | 1 | 6 million | abd. pain, nausea | Not tested | Partial response | Local tumor necrosis on histopathology |
| 2 | 47 IIIC | Ovarian | 1 | 57 million | abd. pain, nausea | No | Mixed response | Resolved ascites before GCV Rx |
| 3 | 59 IIIC | Ovarian | 1 | 56 million | abd. pain | No | Progressive disease | Deceased 15 mos. after treatment |
| 4 | 51 IIIC | Ovarian | 2 | 680 million | abd. pain, fever, nausea, vomiting | Yes | Progressive disease | Deceased 5 mos. after treatment |
| 5 | 62 IIIC | Ovarian | 2 | 700 million | abd. pain, fever, nausea | Not tested | Progressive disease | Deceased 6 mos. after treatment |
| 6 | 66 IIIC | Fallopian | 2 | 840 million | abd. pain, fever | Yes | Minimal response | Deceased 8 mos. after treatment |
| 7 | 73 IV | Ovarian | 3 | 7 billion | abd. pain | No | Progressive disease | Receiving chemotherapy |
| 8 | 60 IIIC | Ovarian | 3 | 6.3 billion | abd. pain | No | Mass lesion (2 cm) regressed, CA125 decreased 70% | CT scan still without disease 21 mos. later; ↑CA125 |
| 9 | 63 IIIC | Ovarian | 3 | 6.2 billion | abd. pain, nausea, vomiting | yes | Progressive disease | Deceased 3 mos. after treatment |
| 10 | 52 IIC | Ovarian | 3 | 5.7 billion | rash, abd. pain | pending | Progressive disease | Receiving chemotherapy |

TABLE 2

VPC Survival in Patient's Peritoneal Cavity and In Vivo HSVtk Gene Transfer in Patients Treated with Escalated Doses of LTKOSN.1 Retroviral VPC.

| Patient number (VPC dose) | Cell source | Day 3 | | | Day 7 | | | Day 14 (pre-GCV treatment) | |
|---|---|---|---|---|---|---|---|---|---|
| | | HSVtk | env | VPC (cfu/ml) | HSVtk | env | VPC (cfu/ml) | HSVtk | env |
| 1 ($1 \times 10^6$ cells/kg) | PW | − | − | − | − | − | − | − | − |
| | TB | NA | NA | NA | NA | NA | NA | | |
| 2 ($1 \times 10^6$ cells/kg) | PW | − | − | − | − | − | − | − | − |
| | TB | NA | NA | NA | NA | NA | NA | | |
| 3 ($1 \times 10^6$ cells/kg) | PW | − | − | − | − | − | − | − | − |
| | TB | NA | NA | NA | NA | NA | NA | | |
| 4 ($10 \times 10^6$ cells/kg) | PW | + | + | − | + | + | − | − | − |
| | TB | NA | NA | NA | NA | NA | NA | + | − |
| 6 ($10 \times 10^6$ cells/kg) | PW | + | + | $1.5 \times 10^6$ | + | + | $1.3 \times 10^6$ | − | ND |
| | TB | NA | NA | NA | NA | NA | NA | + | ND |
| 7 | PW | + | + | − | + | + | − | − | − |

TABLE 2-continued

VPC Survival in Patient's Peritoneal Cavity and In Vivo HSVtk Gene Transfer in Patients Treated with Escalated Doses of LTKOSN.1 Retroviral VPC.

| Patient number (VPC dose) | Cell source | Day 3 | | | Day 7 | | | Day 14 (pre-GCV treatment) | |
|---|---|---|---|---|---|---|---|---|---|
| | | HSVtk | env | VPC (cfu/ml) | HSVtk | env | VPC (cfu/ml) | HSVtk | env |
| (100 × 10⁶ cells/kg) | TB | NA | NA | NA | NA | NA | NA | − | − |
| 8 | PW | + | + | − | + | + | − | − | − |
| (100 × 10⁶ cells/kg) | TB | NA | NA | NA | NA | NA | NA | − | − |
| 9 | PW | + | + | >1 × 10⁶ | + | − | − | + | − |
| (100 × 10⁶ cells/kg) | TB | NA | NA | NA | NA | NA | NA | + | − |
| 10 | PW | + | Pending | − | + | Pending | − | + | Pending |
| (100 × 10⁶ cells/kg) | TB | NA | NA | NA | NA | NA | NA | + | Pending |

Figure 1:
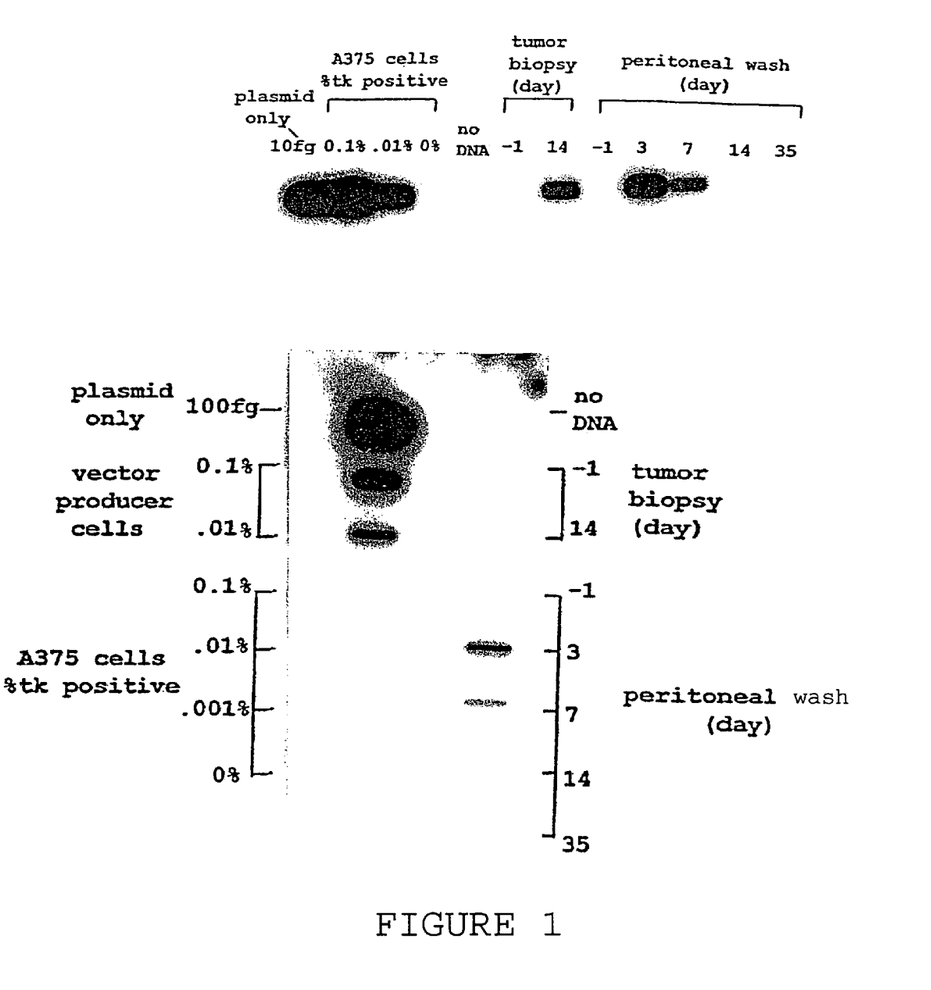

PW: peritoneal wash;
TB: tumor biopsy during laparoscopy;
−: negative;
+: positive;
NA—not applicable;
ND—not done Most patients developed some abdominal pain consistent with peritoneal irritation that lasted for up to 7 days, and 3 patients had low grade fever. One patient exhibited grade 2 nausea and vomiting, otherwise, only grade 1 toxicities were observed. Four of ten evaluatable patients demonstrated some evidence of an antitumor response. One patient had the complete resolution of a 2 cm mass on CT scan and a 70% reduction of CA125. Of the remaining three, one patient had a partial, the second patient a minor, and the third patient showed a mixed response to the treatment. The patient with the mixed response demonstrated significant resolution of malignant ascites prior to GCV infusion, but developed a malignant pleural effusion. Tumor tissues obtained on day +14 prior to GCV were positive for the HSVtk gene by PCR in several patients. Quantitative PCR analysis demonstrated less than 1% gene transfer into intraperitoneal tumor biopsies prior to GCV administration. FIG. 1 shows the results of PCR analysis of peritoneal washes and biopsies conducted on patient 4. The demonstration of tumor regression with only low level gene transfer (<1%) suggests that hyperacute rejection of the murine cells might inhibit the cancer by an innocent bystander effect such as that described for red blood cells (RBC) in penicillin antigen-antibody complex-mediated hemolytic anemia. Schwartz, R. S., Silberstein, L. E. & Berkman, E. M. Autoimmune hemolytic anemia. In *Hemotology Basic Principles and Practice, 2nd* ed. (eds Hoffman, R. et al.) 723–724 (Churchill Livingstone, N.Y., 1995). The penicillin antigen-antibody complexes adhere to the RBC membrane and activate complement against the RBC. The αgal and anti-αgal antigen-antibody may adhere to tumor cells and possibly activate complement and injure the tumor cells. Viable LTKOSN.1 murine VPC were recovered from peritoneal wash samples of patients on day +3 and/or day +7 after infusion at the two highest dose levels. The recovered VPC cultures were G418 resistant, and their supernatants contained high titers of LTKOSN retroviral vector similar to those produced by LTKOSN.1 VPC used for infusion into patients (1–1.5×10⁶ cfu/ml). VPC were detectable by PCR up to day +7, but at day +14 none were detected (FIG. 1).

Example 3

Safety Results

Replication competent retrovirus (RCR) S⁺L⁻ assays were conducted on peripheral blood lymphocytes (PBL) of patients. Cells were co-cultured with *Mus dunni* cells for two weeks (four passages). After two weeks, supernatants were collected and centrifuged. The supernatant was then placed on PG-4 cells (40 to 60% confluent) for two hours. The supernatant was removed and D10 (DMEM, 10% fetal bovine serum, L-glutamine) added. After four to seven days, PG-4 cells were observed for development of foci. MMLV 4070A was used as the positive control, and *Mus dunni* cells alone were used as the negative control. No RCR was present in PBL samples obtained up to one year after VPC infusion as detected in co-cultivation with *Mus dunni* followed by S+L⁻ assay.

Example 4

Sample Treatment and Genomic DNA Isolation

Genomic DNA was isolated from 3 ml of whole blood using the Genomic DNA Purification Kit (Promega or Sigma). Tumors were digested by mincing the tissue and adding tumor lysis solution (2 mg/ml Collagenase, Type II; 0.2 mg/ml DNAaseI; 2.1 μg/ml Hyaluronidase, Type V). The tumor was dissociated on a slow rocker at RT for 1 hour, and cells were collected by filtering through a nylon mesh. The peritoneal wash samples were centrifuged to collect all the cells, and DNA was isolated using the Genomic DNA Isolation Kit (Sigma). Isolation of genomic DNA from A375 LTKOSN.1 cells diluted with A375 NV cells was used to create $10^{-2}$, $10^{-3}$, $10^{-4}$, and $10^{-5}$ cell dilutions for PCR controls.

Example 5

Retroviral Envelope Gene Expression (RCR Detection)

MLVENV-F (5'-ACCTGGAGAGTCACCAACC-3') SEQ ID NO: 1 and MLVENV-R (5'-TACTTTGGAGAG-GTCGTAGC-3') SEQ ID NO: 2 were designed to amplify a 411 bp fragment of the env gene. The PCR reaction was 3 min. at 94° C., followed by 30 cycles of 94° C. for 20 seconds, 68° C. for 1 minute, and 72° C. for 1 minute, with a final extension of 10 minutes at 72° C. The reaction mix was 500 ng of genomic DNA (sample), 25 pmoles of each primer, 1× PCR buffer, 0.2 mM dNTPs, 1.25 MM MgCl$_2$, and 1.25 U Taq. A375 NV cells and a sample containing no genomic DNA were used as negative controls. 100 fg of pPAM3 was used as a positive control for each sample. For the lymphocyte samples, 500 ng of each A375 LTKOSN.1 dilution of genomic DNA ($1\times10^{-4}$ and $5\times10^{-4}$) was used as additional controls. PCR product from blood lymphocytes and controls were transferred to membrane using a slot blot. The env probe was labeled with ($^{32}$P)dCTP by the random priming technique (Boehringer Mannheim). The blots were hybridized overnight at 42° C. in Hybridisol (Oncor) and washed. No env gene sequence was detected by PCR in PBL samples obtained up to one year after VPC infusion.

Example 6

PCR was Performed to Detect HSVtk Gene in PBL and Tumor Biopsy Samples

PCR primers (JMTKO1 5' TAT AGA CGG TCC TCA CGG GAT 3') SEQ ID NO: 3 and JMTKO3 5' TCA TGC TGC CCA TAA GGT AT 3') SEQ ID NO: 4 were designed to amplify a 388 bp fragment of the TK gene. The reaction mix contained 500 ng of genomic DNA sample. A375 NV cells and a sample containing no genomic DNA was used as negative controls. 100 fg of pLTKOSN.1 was used as a positive control for each sample. For the lymphocyte samples, 500 ng of each A375 LTKOSN.1 dilution of genomic DNA ($10^{-2}$, $10^{-3}$, $10^{4}$, and $10^{-5}$) was used as additional controls. 500 ng of $10^{-3}$ and $10^{-4}$ dilutions of A375 LTKOSN.1 genomic DNA were used as controls for the tumor and peritoneal wash cells. PCR product from blood lymphocytes and controls were transferred to membrane using a slot blot. A TK probe was labeled with ($^{32}$P)dCTP by the random priming technique (Boehringer Mannheim). PCR products from peritoneal wash and tumor samples were run out on 1.5% TBE gels and Southern transferred onto nylon membrane following manufacturer's instructions. No HSVtk gene transfer into PBL from patient blood samples up to 3 months after VPC infusion were detected by PCR in any patient.

Example 7

Tracking of Serum anti-αgal Ab Titers

Figure 2:
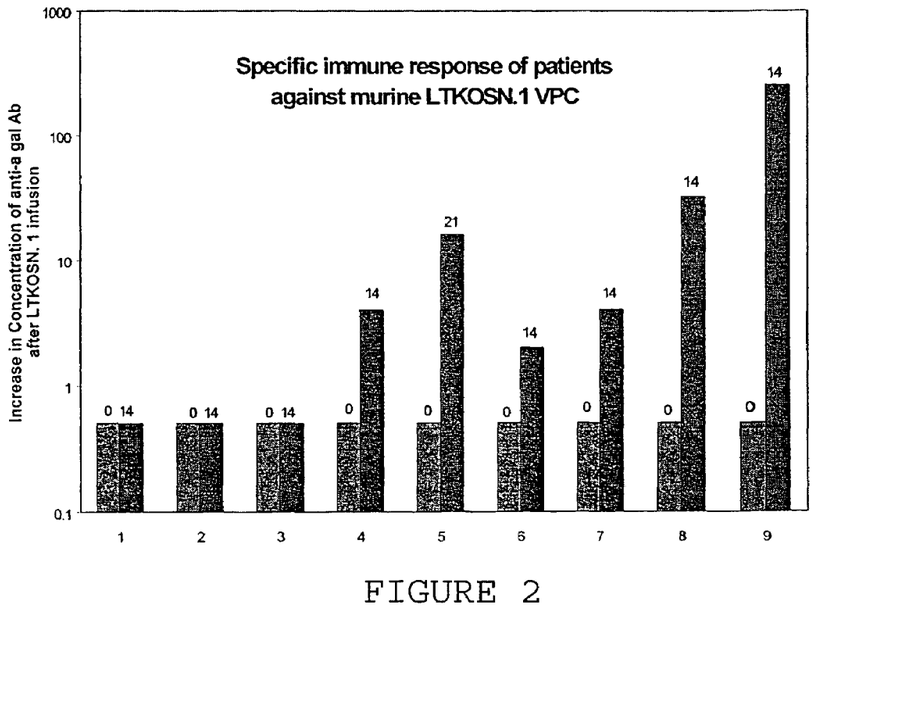
FIG. 2 is a graph showing anti-αgal titer after murine LTKOSN.1 VPC infusion. Data shown for patients 1–9 before (day 0) and on day 14 or 21 after infusion.

Patients' serial blood samples were drawn before VPC infusions and then weekly thereafter. These samples were evaluated by ELISA assay for anti-αgal Ab titers as previously described (FIG. 2). Galili, U., Tibell, A., Samuelsson, B., Rydberg, L. & Groth, C. G. Increased anti-Gal activity in diabetic patients transplanted with fetal porcine islet cell clusters. Transplantation 59, 1549–56 (1995). Plates (96-well) were coated with 1 µg α-gal-BSA per well. Serial dilutions of patient serum samples were used as the primary antibody, and horseradish peroxidase conjugates of anti-human IgG served as the secondary antibody. It was expected that patients who received murine cell xenografts would generate increases in anti-αgal titers. Previously, diabetic patients grafted with fetal porcine islet cells had been noted to develop an increase in anti-αgal titers (8 to 64-fold), while total immunoglobulin concentration was unchanged. Galili, U., Tibell, A., Samuelsson, B., Rydberg, L. & Groth, C. G., Transplantation 59, 1549–56 (1995). Thus, the increase in anti-αgal titer was the result of a specific immune response against αgal epitopes on the xenograft. In the first 3 patients treated with $1\times10^6$ VPC/kg (range 54–57$\times10^6$ VPC), no increases in anti-αgal titers were seen. However, strong and significant response to the αgal antigen was observed at the higher doses. Patients 4 through 9 treated at 10–100$\times10^6$ VPC/kg dose had 2-fold to 256-fold increases in anti-αgal titers by ELISA. No significant difference in concentration of IgG and IgM was found in peripheral blood serum samples obtained prior and on day 14 following murine VPC infusion (data not shown). Thus, the Ab response is a specific anti-αgal immune response. This might be another way to enhance the immune effects against the tumor and break tolerance. Results from this Phase I clinical trial of LTKOSN.1 VPC for women with recurrent ovarian cancer suggest a possible role for hyperacute rejection in antitumor responses in humans.

Example 8

Killing Effect of Patient Serum on LTKOSN.1 Murine VPC in Vitro

Figure 3:
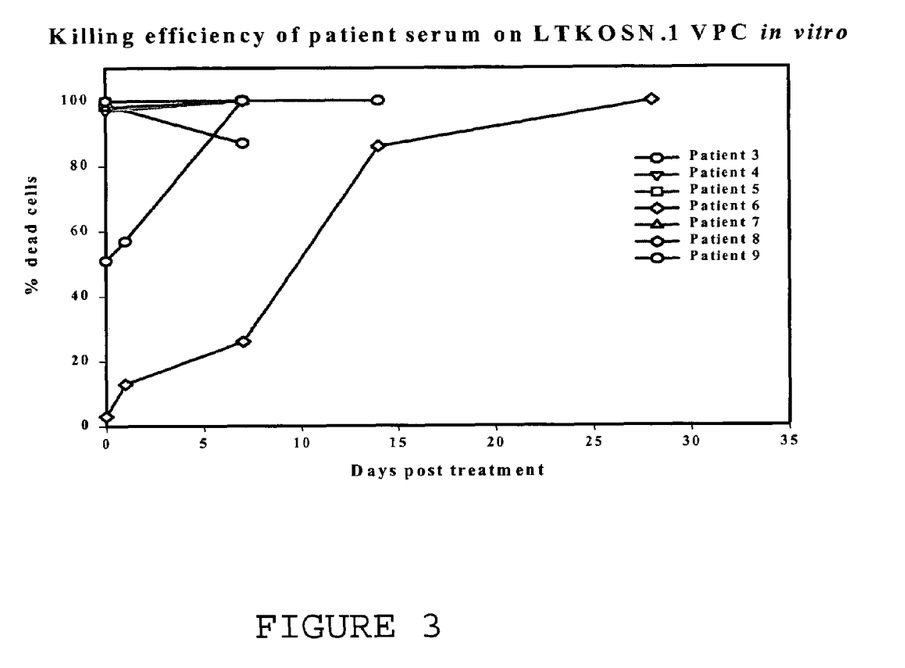
FIG. 3 is a graph showing killing efficiency of patient serum on murine LTKOSN.1 VPC in vitro.

Aliquots of $1\times10^6$ LTKOSN.1 VPC, with viability not less than 95%, were suspended in incubation medium containing 90% of patient serum and 10% of DMEM (Gibco). The cell suspension was incubated at 37° C. for one hour, and cell viability was assessed using trypan blue exclusion. Patient serum inactivated for 30 minutes at 56° C. served as a negative control for complement-dependent murine VPC destruction. Human A375 melanoma cells ($1\times10^6$/aliquot) served as a control for species-specific anti-αgal antibody-mediated cytotoxicity of patients' sera. Serum samples were obtained-prior to and 7 and 14 days post murine VPC infusion. The data demonstrated that serum from 7 out of 9 patients killed nearly 100% of murine VPC in this assay (FIG. 3). By day 28 after the infusion of VPC, all patients' sera killed 100% of murine VPC. Viability of A375 cells was not affected by exposure to human serum. Thus, in all patients, sera alone could destroy murine VPC. These findings also support the contention that bleeding during neurosurgical procedures would kill murine VPC rapidly.

Example 9

Killing Effect of Patient Peritoneal Fluid on LTKOSN.1 Murine VPC in Vitro

Figure 4:
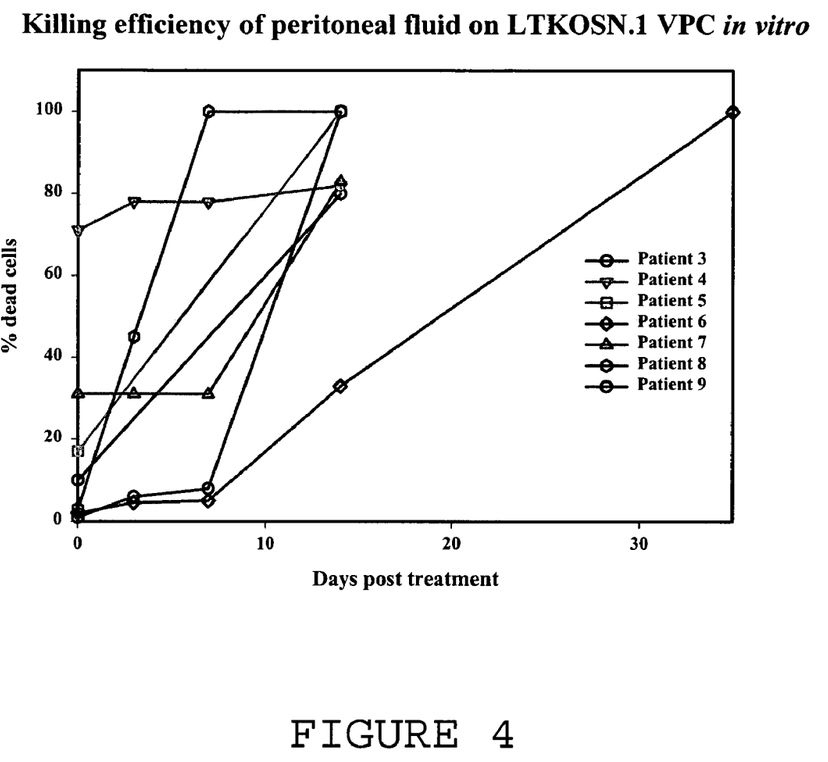
FIG. 4 is a graph showing killing efficiency of patient peritoneal fluid on murine LTKOSN.1 VPC in vitro.

Peritoneal washes were performed during patient evaluation and on days 3, 7, and 14 after VPC infusion. Aliquots of $1\times10^6$ LTKOSN.1 VPC, with viability not less than 95%, were suspended in incubation medium containing 90% of patient peritoneal fluid and tested as above. The results of this analysis over the first 30 days after murine LTKOSN.1 VPC were infused is plotted in FIG. 4. Interestingly, the peritoneal fluid from only one patient initially killed more than 50% of the VPC in this assay. Thus, the pre-existing serum killing ability in the patients (FIG. 3) did not translate into peritoneal fluid that would kill VPC under these ex vivo experimental conditions. However, over than 30 days after murine VPC infusion, the peritoneal fluid was able to mediate high level VPC killing. We have been able to show that the anti-αgal titer increases in the peritoneal cavity after VPC infusion (data not shown). Little detectable IgG was present in the peritoneal fluid in most patients before the xenotransplant; however, the total IgG in the peritoneal cavity increased dramatically in four of six patients tested. This suggests that the anti-αgal Ab response to murine cells altered the physiology of the peritoneal cavity. These findings correlate with the timing of the observed antitumor responses. For example, patient #8 who manifested the best and most durable antitumor response observed had a high induced serum titer of anti-αgal Ab (32-fold increase) and a rapid up-slope in the ability of her peritoneal fluid to kill murine VPC in the ex vivo assay. These data support a correlation between anti-αgal immunity and tumor response, but in this Phase I trial GCV was administered 14 days after VPC, and this temporal overlap makes conclusions about causation difficult. The proposed trial design of waiting 4 weeks after VPC infusion to treat with GCV may allow these effects to be separated. Changes in the peritoneal cavity may alter the ability of the immune system to detect these tumors.

Example 10

Characterization of LTKOSN.1 VPC Obtained from Peritoneal Washes

Peritoneal wash samples were centrifuged at 250×g, and the cell pellets were resuspended in DMEM supplemented with 10% FBS (Gibco) and aliquoted. One mg/ml of G418 (Gibco) was added to one aliquot, and cells were incubated at 37° C., 5% $CO_2$. Cells in samples containing VPC reached confluency in approximately 10 days after cell culture initiation. Cells were cultured in medium containing one mg/ml G418 for two additional weeks, then the supernatant was used to infect IGROV human ovarian carcinoma cells in standard vector titration assay as established at our Institute. The data on the recovered VPC is shown in Table 2 and clearly demonstrates that high titer VPC can be recovered up to 7 days after intraperitoneal infusions.

Example 11

Anti-fetal Bovine Serum Response

Figure 5:
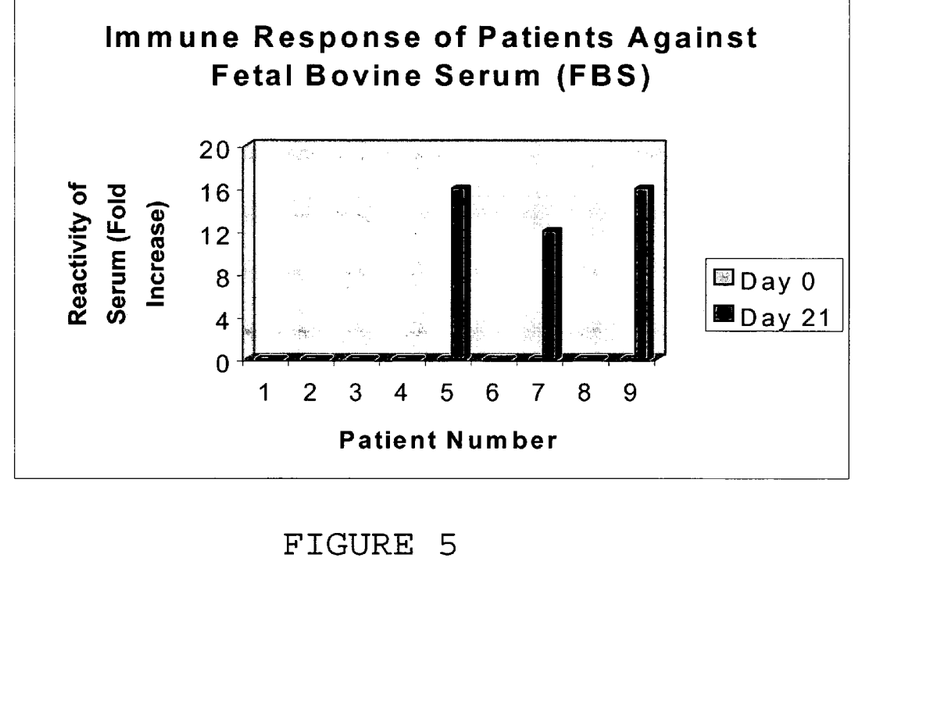
FIG. 5 is a graph showing the increase in reactivity of patient's serum against fetal bovine serum (FSB) following murine VPC LTKOSN.1 infusion (fold).

The humoral immune response to fetal bovine serum (FBS) was also tested (FIG. 5). ELISA for anti-FBS was performed in Nuclon 96-well plates were coated with BSA by filling wells with 100 μl of 5% BSA in PBS and incubating at 4° C. overnight. The plate was washed four times with PBS, and 150 μl of blocking buffer (1% dry milk; 0.1% SDS) was added and incubated at room temperature for one hour. Primary antibody (100 μl diluted patient serum (1:50) samples followed by serial dilution) was added following 4 washes and incubated for one hour. After four washes, 150 μl of blocking buffer was added, and the plate was incubated two hours. The secondary horseradish peroxidase-conjugated antibody [100 μl of antibody; 1/40,000 dilution of goat anti-human (Pierce) for patient samples; 1/15,000 dilution of goat anti-bovine (Kirkegaard & Perry) for positive control] was added and incubated for one hour. Following four washes, 100 μl of room temperature TMB (Sigma) substrate was added and color was allowed to develop for 15 minutes. The reaction was stopped by adding 100 μl of 1 M $H_2SO_4$. Absorbance values were read at 450 nm on and ELISA plate reader. Only 3 patients developed anti-FBS Ab (out of 9 tested).

Example 12

Human Tumor Cell Clones Susceptible to Serum Killing Express αgal

To demonstrate the significance of α(1,3)GT, our group has previously demonstrated that the retroviral transfer ofα(1,3)GT into tumor cells can induce sensitivity to normal human serum. Human tumors are not sensitive to lysis by autologous human serum. A truncated version of the murine α(1,3)GT enzyme was cloned into the LNCX retroviral vector backbone. Larsen, R. D., Rajan, V. P., Ruff, M. M., Kukowska-Latallo, J., Cummings, R. D., and Lowe, J. B. Isolation of a cDNA encoding a murine UDPgalactose:beta-D-galactosyl-1,4-N-acetyl-D-glucosaminide alpha-1,3-galactosyltransferase: expression cloning by gene transfer Proc. Natl. Acad. Sci. U.S.A. 86(21), 8227–31 (1989); Miller, A. D. & Buttimore, C. Redesign of retrovirus packaging cell lines to avoid recombination leading to helper virus production Molec. Cell Biol. 6, 2895–2902 (1986). This eukaryotic expression vector was transfected into human A375 melanoma tumor cells that were then exposed to human serum. Many A375 subclones were obtained, and data for three representative examples are presented. Clones A375αG.7 and A375αG.8 showed significant sensitivity to serum killing while clone A375αG.11 did not (Table 3).

TABLE 3

Effect of human serum on A385αG cells.

| Cell line | Human serum % viable | Human serum + sCR1 % viable | Human serum Heat inactivated % viable | αgal expression by FACS |
|---|---|---|---|---|
| A375 | 98.7 | Not done | 96.9 | − |
| A375αG.7 | 2.6 | 92.0 | 93.9 | + |
| A375αG.8 | 11.1 | 91.6 | 95.5 | + |
| A375αG.11 | 96.2 | Not done | Not done | − |

Incubation with sCR1 prevented cell killing by serum. The sensitive clones A375αG.7 and A375αG.8 expressed αgal by FAGS analysis, while clone A375αG.11 did not exhibit the epitope. These data show that the presentation of αgal alone on human tumor cells induces sensitivity to human serum.

Investigators have demonstrated that certain types of lectins bind specifically to αgal on glycoproteins or glycolipids. Wood, C., Kabat, E. A., Murphy, L. A. & Goldstein, I. J. Immunochemical studies on the combining site of two isolectins A4 and B4 isolated from Bandeirea simpliciflia Arch. Biochem. Biophys. 198, 1–11 (1979). This method was used to quantify the amount of αgal present on cells using *Griffonia simplicifolia* isolectin B4 (Vector Laboratories, Burlingame, Calif.) and analyzed by COULTER FRCS analyzer. The presence of αgal epitopes correlated with sensitivity to human serum for the A375αgal clones. The next step in acquiring evidence needed to pursue this strategy was to demonstrate in vivo differences in an animal model. This presented a problem since murine cells contain an intact α(1,3)GT gene. So, we injected original A375 cells and A375 cells expressing αgal into athymic nude mice after brief (30 min) exposure to human serum ex vivo. Animals were monitored for tumor growth for up to 28 days. Only animals injected with A375αG.7 cells exposed to human serum and irradiated A375 cells (positive control) were tumor free. The α(1,3)GT gene can also sensitize cells to normal human serum when transferred by a Herpes simplex vector into ovarian or colon carcinoma cells.

Example 13

Eosinphilia Occurs within the Peritoneal Cavity after Xenotransplants in Humans

Figure 6:
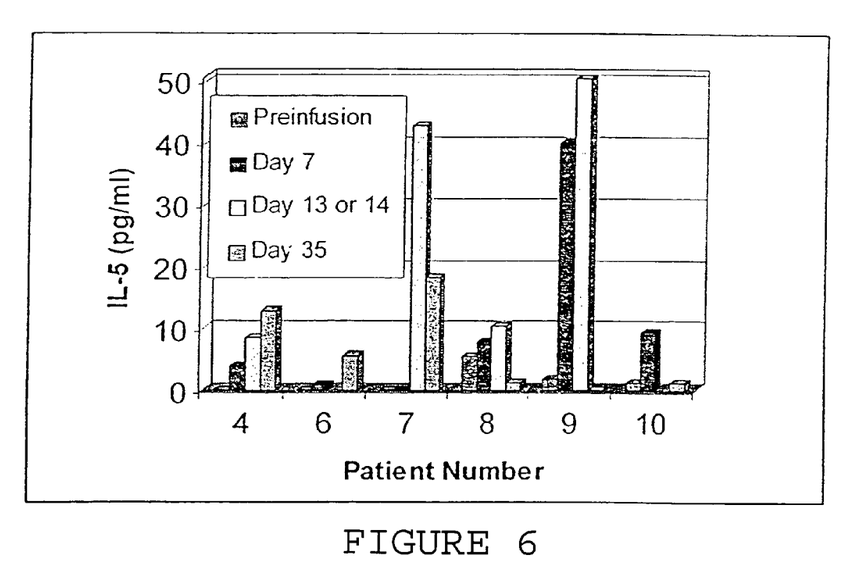
FIG. 6 is a graph of levels of IL-5 in peritoneal fluid after murine LTKOSN.1 VPC infusion. ELISA assay was performed to measure the levels of IL-5 from peritoneal washing samples both before and after murine VPC infusions. Peak levels of IL-5 were found 7 to 14 days after VPC infusion. This IL-5 response overlaps closely the period during which immune destruction and elimination of the cells occurs.

One striking finding in patents was the development of eosinophilia in the peripheral blood and the peritoneal cavity during time of xenograft rejection (FIG. 6). The peripheral blood eosinophil count increased on average by 87% by day 14 after murine cells administration. Intraperitoneal washing cell counts demonstrated a mean of 15% (5–28%) and 13% (1–33%) eosinophils on days 7 and 14, respectively. Eosinophils may be important immune effector cells against xenogeneic cells transplanted into humans. In addition, the level of interleukin-5 (IL-5) was measured in samples of peritoneal fluid from patients both before and after the infusion of xenogeneic cells. These data represent an interesting basis for hypothesis development concerning changes in the immune physiology of the peritoneal cavity that may lead to immune mediated destruction of ovarian cancer.

Example 14

Phase II Trial

The Phase II trial will involve 43 adult women with recurrent or refractory ovarian, fallopian, or peritoneal carcinoma, will be evaluated for the extent and location(s) of their disease before being entered into the study. Patients will have a CT scan and laparotomy or laparoscopy with biopsy to confirm the diagnosis. During laparoscopy, eligible patients will have a peritoneal dialysis catheter placed. HSVtk VPC will be infused into the peritoneal space over 15-60 minutes in a total volume of one to two liters of plasmalyte. Four weeks later, GCV will be administered over one hour at 5 mg/kg/dose IV b.i.d. for 14 days. Patients may receive up to three cycles of therapy if no tumor regression is observed. After the completion of therapy, patients who continue to show evidence of response will be followed every three months for the first year.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for treating a solid tumor in a human subject, the method comprising:
   administering to the subject and at or near the solid tumor an effective amount of xenogeneic retroviral vector producer cells having α(1,3)galactosyl epitopes to activate a hyperacute rejection response, wherein administration of said vector producer cells is not followed by treatment with ganciclovir.

2. The method of claim 1, wherein the tumor is in the peritoneal cavity.

3. The method of claim 1, wherein the xenogeneic cells are murine cells.

4. The method of claim 1, wherein the solid tumor is the result of a carcinoma selected from the group consisting of ovarian carcinoma, fallopian carcinoma, and peritoneal carcinoma.

5. The method of claim 1, wherein said activation of a hyperacute rejection comprises administering xenogeneic cells from a mammal expressing α(1,3)galactosyl epitopes to said subject.

6. A method for treating a solid tumor in the peritoneal cavity of a human subject having pre-existing anti-αGal antibodies, the method comprising:
   administering to the subject and at or near the solid tumor an effective amount of murine retroviral vector producer cells having α(1,3)galactosyl epitopes, wherein said amount activates a hyperacute rejection response against said xenogeneic cells and an innocent bystander immune response against tumor cells, thereby inhibiting the growth of a tumor in the subject wherein administration of said vector producer cells is not followed by treatment with ganciclovir.

7. The method of claim 6, wherein the solid tumor is the result of a carcinoma selected from the group consisting of ovarian carcinoma, fallopian carcinoma, and peritoneal carcinoma.

8. A method for inhibiting the growth of a solid tumor in a human subject having pre-existing anti-αGal antibodies, the method comprising: delivering into or near the solid tumor an effective amount of a murine retroviral vector producer cells that expresses α(1,3)galactosyl epitopes thereby causing a local hyperacute rejection response against said xenogeneic cells and a bystander immune reaction against the tumor in the absence of ganciclovir thereby inhibiting the growth of the tumor in the subject, wherein administration of said vector producer cells is not followed by treatment with ganciclovir.

* * * * *